(12) United States Patent
Basta (10) Patent No.: US 11,864,959 B2
(45) Date of Patent: Jan. 9, 2024

(54) SURGICAL GUIDES

(71) Applicant: Orthosoft ULC, Montreal (CA)

(72) Inventor: Ian Basta, Montreal (CA)

(73) Assignee: Orthosoft ULC, Montreal (CA)

( * ) Notice: Subject to any disclaimer, the term of this patent is extended or adjusted under 35 U.S.C. 154(b) by 88 days.

(21) Appl. No.: 17/379,419

(22) Filed: Jul. 19, 2021

(65) Prior Publication Data

US 2022/0015861 A1 Jan. 20, 2022

Related U.S. Application Data

(60) Provisional application No. 63/054,040, filed on Jul. 20, 2020.

(51) Int. Cl.
*A61B 90/50* (2016.01)
*A61B 17/17* (2006.01)
(Continued)

(52) U.S. Cl.
CPC ............ *A61B 90/05* (2016.02); *A61B 17/176* (2013.01); *A61B 17/15* (2013.01); *A61B 2017/568* (2013.01); *A61C 1/082* (2013.01)

(58) Field of Classification Search
CPC ....... A61B 90/50; A61B 17/176; A61B 17/15; A61B 2017/568; A61C 1/082
See application file for complete search history.

(56) References Cited

U.S. PATENT DOCUMENTS

2010/0087829 A1* 4/2010 Metzger ............. A61B 17/1675
606/96

2011/0015636 A1* 1/2011 Katrana ............. A61B 17/1739
606/80
(Continued)

FOREIGN PATENT DOCUMENTS

| CA | 2931344 A1 | 5/2015 | |
| CA | 3122429 A1 | 6/2020 | |
| WO | WO-2020124007 A1 * | 6/2020 | ............. A61B 17/17 |

OTHER PUBLICATIONS

"Canadian Serial No. 3,124,915, Examiner's Rule 86(2), Report Mailed Nov. 2, 2022, 7 pgs.", 17 pgs.
(Continued)

*Primary Examiner* — Kevin T Truong
*Assistant Examiner* — Diana Jones
(74) *Attorney, Agent, or Firm* — SCHWEGMAN LUNDBERG & WOESSNER, P.A.

(57) ABSTRACT

Disclosed herein are surgical guides, surgical supports, surgical systems, and methods of use thereof. The surgical guides, supports, and systems discloses herein can include an instrument and a patient-specific support. The instrument can be connectable to a surgical support arm and include a guide surface. The patient-specific support can comprise an instrument engagement portion and an anatomy contacting surface. The instrument engagement portion can be configured to receive a portion of the instrument and the anatomy contacting surface contoured to match a contour of an anatomical surface of a patient. When coupled to the patient-specific support, the surgical support arm and the patient-specific support can position the instrument and the guide surface in a predetermined location and orientation relative to the anatomical surface of the patient with increased stability.

13 Claims, 9 Drawing Sheets

(51) Int. Cl.
*A61C 1/08* (2006.01)
*A61B 17/15* (2006.01)
*A61B 17/56* (2006.01)
*A61B 90/00* (2016.01)

(56) References Cited

U.S. PATENT DOCUMENTS

| | | | |
|---|---|---|---|
| 2016/0374697 A1* | 12/2016 | Kehres | A61B 17/15 606/87 |
| 2017/0071677 A1* | 3/2017 | Utz | A61B 34/20 |
| 2018/0085133 A1* | 3/2018 | Lavallee | A61B 17/1764 |
| 2019/0150958 A1* | 5/2019 | Kehres | A61B 17/15 |

OTHER PUBLICATIONS

"Canadian Serial No. 3,124,915, Response filed Feb. 7, 2023 to Examiner's Rule 86(2) dated Nov. 2, 2022", 16 pgs.

* cited by examiner

SURGICAL GUIDES

CLAIM OF PRIORITY

This application claims the benefit of U.S. Provisional Patent Application Ser. No. 63/054,040, filed on Jul. 20, 2020, the benefit of priority of which is claimed hereby, and which is incorporated by reference herein in its entirety.

FIELD OF THE DISCLOSURE

The present invention relates generally to supported surgical instruments and use thereof.

BACKGROUND

Some surgical procedures include use of a variety of instruments. In some of these procedures, it is required that instruments, such as a retractor, be maintained in a single position for an extended period of time, such as an hour or more. During this time, other instruments can be used to perform other aspects of the surgery.

SUMMARY

The following, non-limiting examples, detail certain aspects of the present subject matter to solve the challenges and provide the benefits discussed herein, among others.

Example 1 is a surgical system comprising: an instrument including a guide surface, the instrument coupled to a distal end of a surgical support arm; and a patient-specific support comprising an instrument engagement portion and an anatomy contacting surface, the instrument engagement portion configured to receive a portion of the instrument and the anatomy contacting surface contoured to match a contour of an anatomical surface of a patient, wherein, when coupled to the patient-specific support, a surgical support arm and the patient-specific support position the guide surface of the instrument in a predetermined location and orientation relative to the anatomical surface of the patient with increased stability in comparison to the surgical support arm holding the instrument alone.

In Example 2, the subject matter of Example 1 optionally includes wherein the instrument engagement portion comprises a channel sized to receive the portion of the instrument.

In Example 3, the subject matter of any one or more of Examples 1-2 optionally include wherein the instrument engagement portion includes a tab and the portion of the instrument includes a protrusion, the tab sized to engage the protrusion.

In Example 4, the subject matter of any one or more of Examples 1-3 optionally include wherein the instrument engagement portion includes a plurality of protrusions arranged to engage the portion of the instrument.

In Example 5, the subject matter of any one or more of Examples 1-4 optionally include wherein the instrument engagement portion defines a through hole sized to receive a drill guide.

In Example 6, the subject matter of any one or more of Examples 1-5 optionally include wherein the instrument engagement portion defines a slot sized to receive a cut guide.

In Example 7, the subject matter of any one or more of Examples 1-6 optionally include wherein the anatomy contacting surface forms a lip sized to engage a portion of the anatomical surface.

In Example 8, the subject matter of any one or more of Examples 1-7 optionally include wherein the patient-specific support defines a cut slot.

In Example 9, the subject matter of any one or more of Examples 1-8 optionally include the surgical support arm.

In Example 10, the subject matter of any one or more of Examples 1-9 optionally include wherein the guide surface of the instrument defines a cut slot.

In Example 11, the subject matter of any one or more of Examples 1-10 optionally include wherein the patient-specific support further comprises a second instrument engagement portion.

In Example 12, the subject matter of Example 11 optionally includes a second surgical support arm; a second instrument connectable to the second surgical support arm and the second instrument engagement portion.

In Example 13, the subject matter of any one or more of Examples 1-12 optionally include wherein the anatomy contacting surface is contoured to engage teeth.

In Example 14, the subject matter of any one or more of Examples 1-13 optionally include wherein the anatomy contacting surface is contoured to engage a mandible.

In Example 15, the subject matter of any one or more of Examples 1-14 optionally include wherein the anatomy contacting surface is contoured to engage a long bone.

Example 16 is a surgical system comprising: a surgical support arm including a cut guide holder, the surgical support arm including a plurality of lockable joints configured to maintain a position of a distal end of the surgical support arm; and a patient-specific cut guide including a surgical support arm interface, a guide surface, and an anatomy contacting surface, the surgical support arm adapted to receive the patient-specific cut guide, the anatomy contacting surface contoured to match a contour of an anatomical surface of a patient, wherein, when coupled to the surgical support arm interface, the surgical support arm in combination with the anatomy contacting surface position the guide surface in a predetermined location and orientation relative to an anatomical feature of the patient with increased stability in comparison to the patient-specific cut guide or surgical support arm supporting the guide surface alone.

In Example 17, the subject matter of Example 16 optionally includes wherein the surgical support arm interface defines a slot sized to receive the cut guide holder.

In Example 18, the subject matter of any one or more of Examples 16-17 optionally include wherein the surgical support arm interface defines a circular opening sized to receive the cut guide holder.

In Example 19, the subject matter of any one or more of Examples 16-18 optionally include wherein the cut guide holder includes a protrusion that extends from an instrument body and the surgical support arm interface includes a tab sized to engage the protrusion.

In Example 20, the subject matter of any one or more of Examples 16-19 optionally include wherein the patient-specific cut guide comprises a plurality of body portions connected via respective bridge members, the plurality of body portions and the bridge members form a plurality of slots.

In Example 21, the subject matter of any one or more of Examples 16-20 optionally include wherein the anatomy contacting surface forms a lip sized to engage a portion of the anatomical surface.

In Example 22, the subject matter of any one or more of Examples 16-21 optionally include a second surgical support arm including a second cut guide holder, the patient-specific cut guide including a second surgical support arm interface adapted to receive the second cut guide holder.

Example 23 is a method comprising: fabricating a patient-specific support comprising an instrument engagement portion and an anatomy contacting surface, the anatomy contacting surface contoured to match a contour of an anatomical surface of a patient; attaching the patient-specific support to an anatomy of the patient such that the anatomical contacting surface contacts the anatomical surface of the patient; and attaching an instrument to the instrument engagement portion, the instrument attached to a surgical support arm, wherein attaching the instrument to the instrument engagement portion results in a guide surface of the instrument being positioned in a predetermined location and orientation relative to the anatomical surface of the patient with increased stability in comparison to the patient-specific support or surgical support arm supporting the guide surface alone.

In Example 24, the subject matter of Example 23 optionally includes locking the surgical support arm into a fixed position.

In Example 25, the subject matter of any one or more of Examples 23-24 optionally include attaching a second instrument to a second instrument engagement portion.

In Example 26, the subject matter of any one or more of Examples 23-25 optionally include collecting image data, the image date including contour data for the anatomical surface of the patient; and designing the patient-specific support and the anatomical contacting surface using the contour data.

In Example 27, the subject matter of any one or more of Examples 23-26 optionally include cutting or drilling the anatomy of the patient using the guide surface of the instrument.

In Example 28, the surgical systems or methods of any one or any combination of Examples 1-27 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

In some surgical procedures, it is a requirement to hold instruments, such as a retractor, a drill guide, or a saw guide, in a single position for an extended period of time. As disclosed herein, in these procedures, adjustable mechanical and/or electromechanical arms are often used to hold the instrument in position while other aspects of the procedure are performed. For example, while a hole is drilled in bone or a bone saw is used to cut bone, adjustable mechanical and/or electromechanical arms can be used to hold drill guides or saw guides in place. However, in certain situations and procedures these surgical support arms can lack sufficient stiffness or accuracy to maintain the desired positioning relative to the patient (e.g., minimize movement).

This disclosure provides a solution for minimizing movement of guides by incorporating a patient specific guide that is usable with an adjustable surgical support arm (also referenced as an adjustable arm). The patient specific guide can include surfaces that are contoured to the patient's bone or other anatomical features. As a result, the surfaces of the guide and the patient's anatomy can have increased contact surface area. The surgical support arm in combination with a patient specific guide can provide a dramatic increase in stability of the guide in reference to the patient and improve accuracy of the procedure. The surgical support arm in combination with the patient-specific guide improve accuracy and stability while also allowing the surgeon the free use of both hands, as compared to use of either a surgical support arm or patient-specific cut guide alone.

The guides disclosed herein can be made of plastic and metallic instruments can be assembled intra operatively by the users or during manufacturing of the guides in order to reduce debris generation and guide deformation caused by overheating. For example, cut slots can be used for resections and osteotomy guides and metallic bushings can be used for drill and pin guides.

By utilizing the guides disclosed herein, obstruction of user movement and invasiveness to patients can be minimized. In addition, surgery time and personnel needed can be decreased due to surgical support arms being used to hold the guides in place.

As disclosed herein, guides can be patient specific and 3D printed. The guiding features for cuts, osteotomies, implant pilot holes, etc. can be placed for patient specific needs. Non-limiting applications can include patient specific guides printed for procedures involving cranial, maxillo-facial, knee, ankle, femoral/humeral head resection, etc., to be used in conjunction with surgical support arms such as Walter-Lorenz® surgical assist arms produced by Zimmer Biomet of Warsaw, Indiana.

As disclosed herein, 3D printed patient specific guides can be assembled with reusable instrumentation adapted for surgical assist arms. The patient specific guides can include surfaces that are contoured for a patient's specific anatomical geometry. The guides can further include features sized to receive drill bits, saws, guide rods, etc. and positioned in patient specific locations.

As disclosed herein, reusable metallic cut guides and drill guide attachments that can be part of the surgical support arms and can be attached to the patient specific guides. For example, the surgical support arms can be locked into position once the unique fit is provided by the patient specific surface is obtained. By using the surgical support arms to hold the patient specific guides in place, surgeons can perform the osteotomy without using fasteners to secure cut or drill guides on the bone. For example, a patient specific guide can be positioned on a mandible and held in position with the surgical support arms, which is faster and less invasive. In other applications, such as surgery performed on a fibula or humerus, the patient specific guide can be attached to the bone.

The above discussion is intended to provide an overview of subject matter of the present patent application. It is not intended to provide an exclusive or exhaustive explanation of the invention. The description below is included to provide further information about the present patent application.

As used herein, the terms "proximal" and "distal" should be given their generally understood anatomical interpretation. The term "proximal" refers to a direction generally toward the torso of a patient or base or handle of a tool or instrument, and "distal" refers to the opposite direction of proximal, i.e., away from the torso of a patient or toward the working end of the tool.

Figure 1:
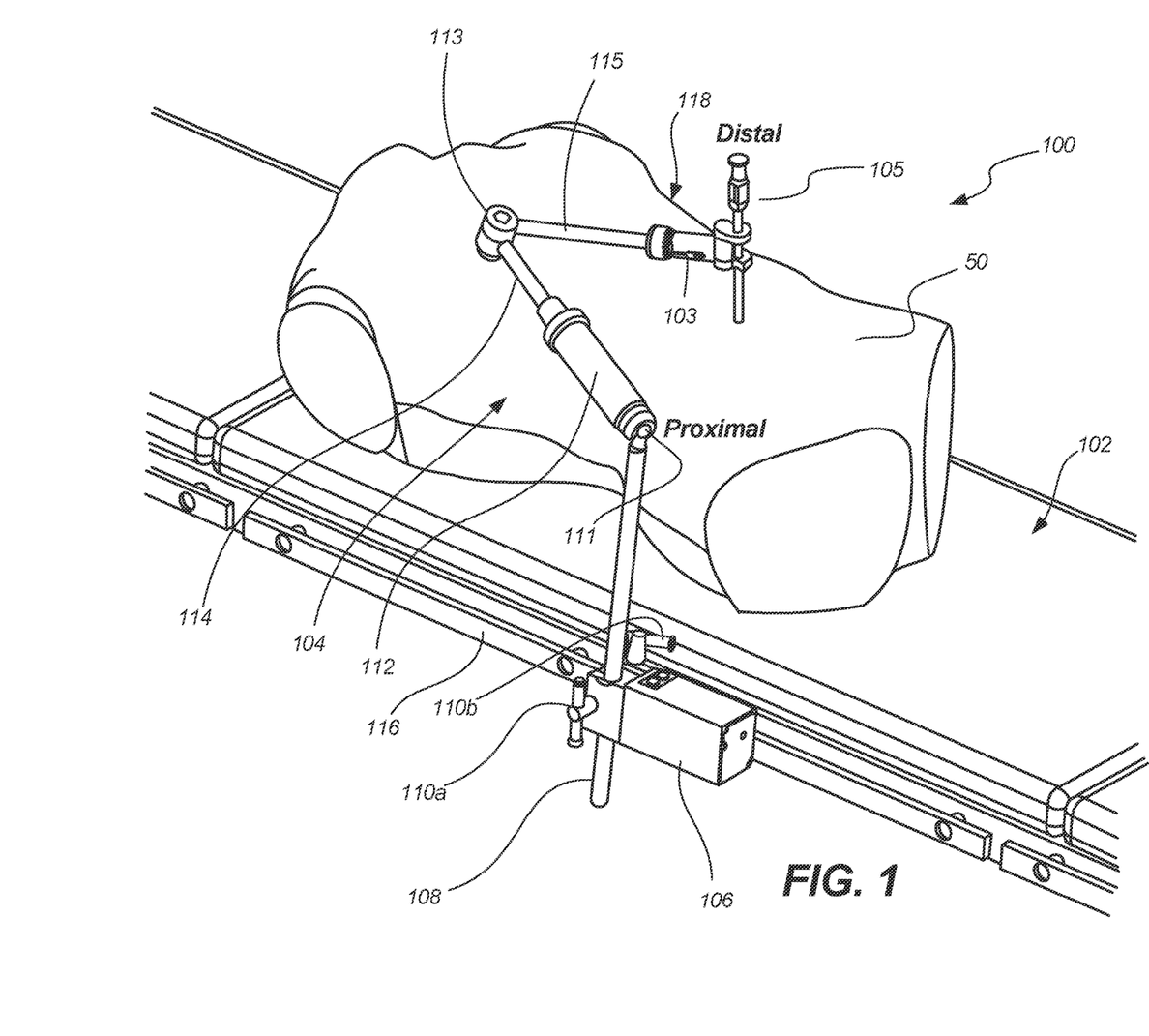
FIG. 1 shows a repositionable, lockable surgical arm, in accordance with at least one example of this disclosure.

FIG. 1 illustrates a perspective view of a repositionable, lockable surgical arm system 100, in accordance with at least one example of this disclosure. Lockable surgical arm system 100 can include a table 102, an arm 104, a tool (or instrument) 105, and a base unit 106. Table 102 can include a rail 116. Base unit 106 can include a pole 108 and a manual clamp 110. Arm 104 can include a proximal joint 111, an actuator unit 112, a distal joint 113, a proximal arm 114, a distal arm 115, and an instrument holder 118. Also shown in FIG. 1 are orientation indicators Proximal and Distal (shown and discussed with respect to arm 104).

Base unit 106, which can include power control circuit components for an electrically powered actuator (such as actuator 112), can be secured to rail 116 of surgical table 102 using, for example, a clamp. Manual clamp 110a of base unit 106 can be operated to tighten base unit 106 against railing 116 and manual clamp 110b can be operated for adjustment of pole 108 to set a height of arm 104 above surgical table 102.

Actuator unit 112 of arm 104 can be located near a proximal end of arm 104 and can be coupled to pole 108 at proximal joint 111. Actuator 112 can also be coupled to a proximal portion of proximal arm 114. Proximal arm 114 can be coupled to actuator 112 via a joint or as an actuatable part of actuator 112 in other examples. Distal arm 115 can be coupled to a distal portion of proximal arm 114 via distal joint 113. Instrument holder or end effector coupler 118 can connect instrument 105 to the distal end of arm 104. In some examples, a lock/unlock button 103 can be provided on or near end effector coupler 118.

The arms of lockable surgical arm system 100 can comprise a serial linkage of arm segments joined by spherical and/or rotational joints. Each of joints 111 and 113 (and any other joints in other examples) can be pivotable and/or rotational joints allowing movement of connected components with one or more degrees of freedom. Joints 111 and 113 (and joints within actuator 112) can be locked and unlocked using base unit 106 and actuator 112, which can be an electric bilateral actuator. In some examples, the joints of the arm can be locked and unlocked with a hydraulic system.

While only proximal arm 114 and distal arm 115 are shown in FIG. 1, additional arm segments can be provided between actuator 112 and end effector coupler 118. Each additional arm segment may require one or more additional joints to form a repositionable, lockable support arm structure. Such additional arm segments can provide greater coverage and ability for the arm to be positioned with more degrees of freedom in the surgical field.

In operation of some examples, the lock/unlock button 103 can be operable by a user to initiate power locking and unlocking of arm 104. When the lock/unlock button 103 is not depressed arm 104 can be in a locked state where joints 111 and 113 are locked such that proximal arm 114 and distal arm 115 cannot move relative to each other or to table 102. When the lock/unlock button 103 is pressed, actuator 112 can unlock joints 111 and 113 such that end effector coupler 118 can be positioned, as desired, and as guided by joints 111 and 113 and proximal arm 114 and distal arm 115. That is, end effector coupler 118 can be moved to a desired position relative to a body 50 through movement paths limited by the freedom of arm 104 to position instrument 105 to a desired position relative to body 50.

Figure 2:
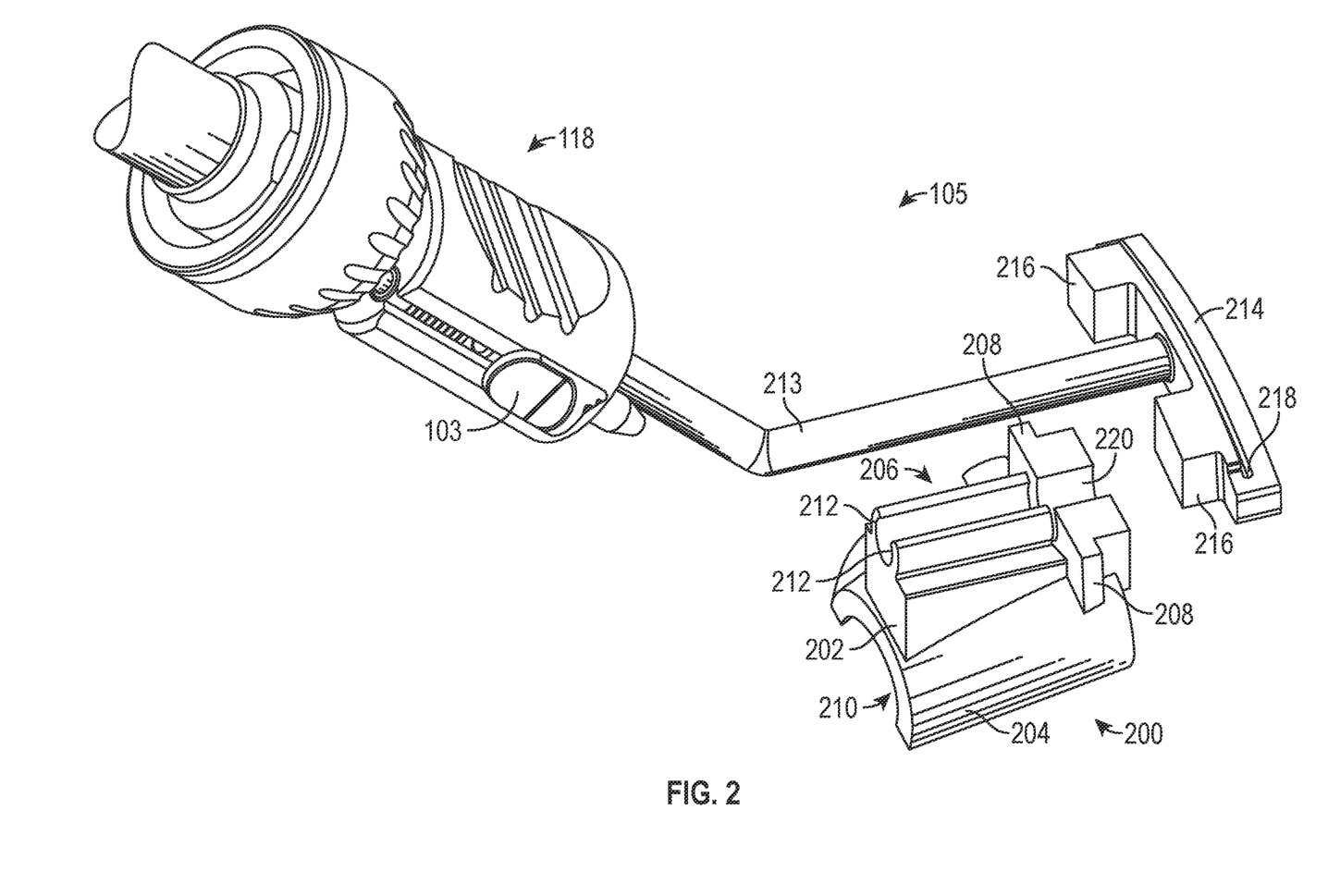
FIG. 2 shows a guide in accordance with at least one example of this disclosure.

FIG. 2 discloses a support 200 in accordance with at least one example of the present disclosure. Support 200 can include a body portion 202, an anatomy contacting portion 204, an instrument engagement portion 206, and one or more tabs 208. Anatomy contacting portion 204 can include an anatomy contacting surface 210. Instrument engagement portion 206 can include one or more protrusions 212.

Figure 3A:
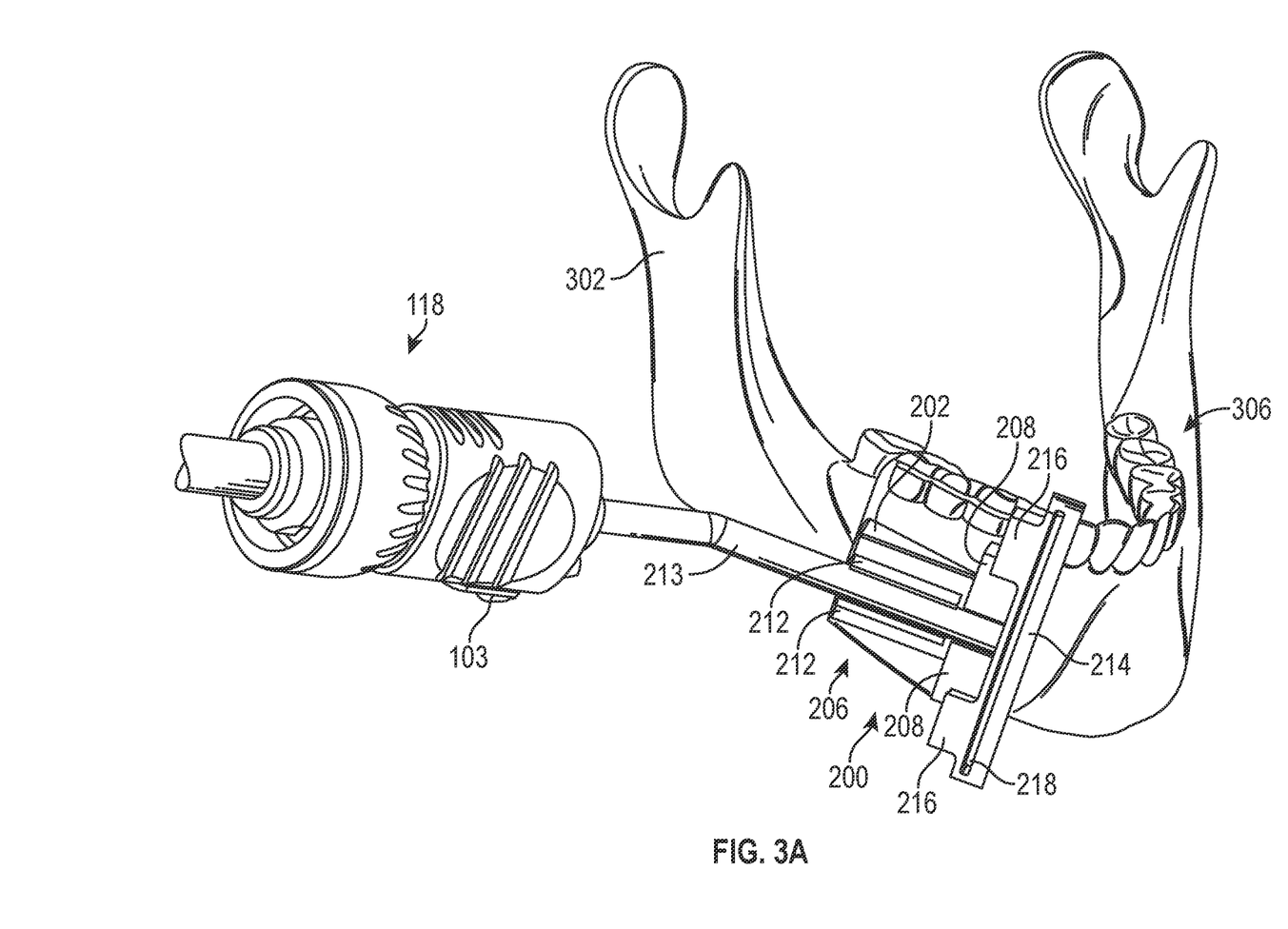
FIGS. 3A and 3B each show the guide from FIG. 2 attached to a bone in accordance with at least one example of this disclosure.
Figure 3B:
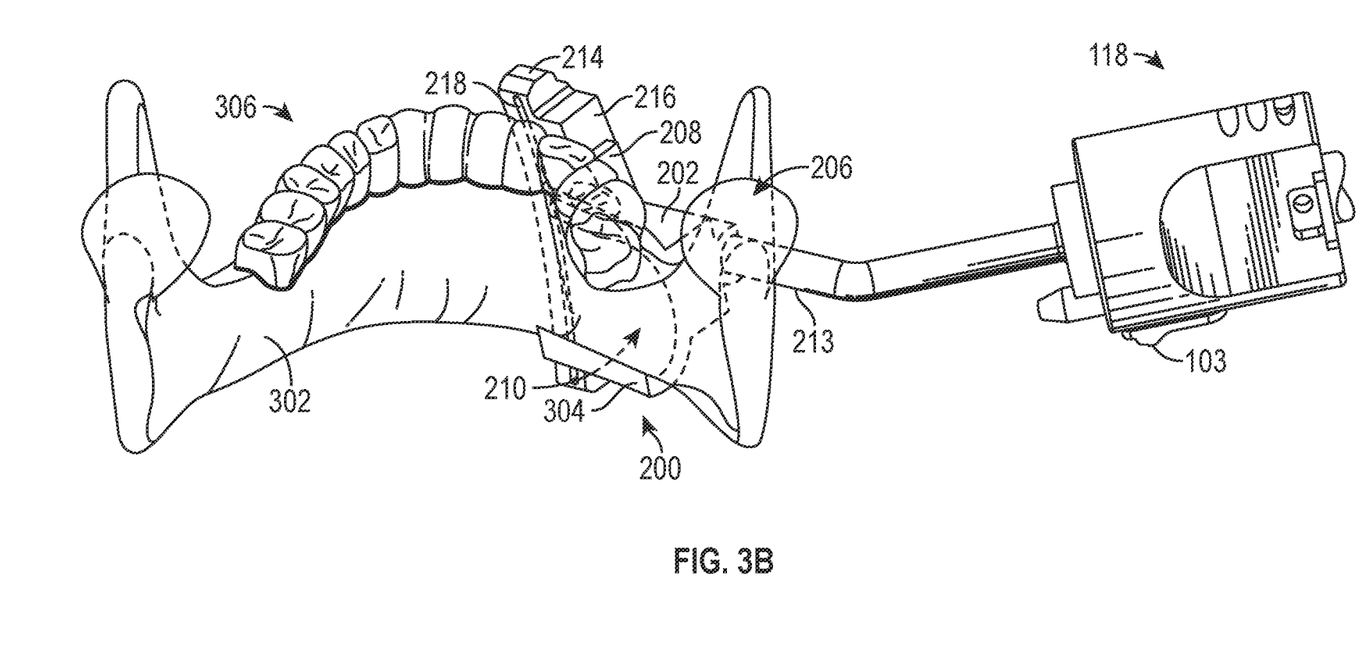

FIGS. 3A and 3B each show support 200 attached to a bone 302 in accordance with at least one example of the present disclosure. As shown in FIGS. 3A and 3B support 200 can attach to bone 302, such as a mandible. Anatomy contacting surface 210 can include one or more indentations and or otherwise curved surfaces that allow anatomy contacting surface 210 to conform to one or more features of bone 302. For example, anatomy contacting surface 210 can form a lip 304 that allows support 200 to contact a lower portion of bone 302. Anatomy contacting surface 210 can also include indentations or other contours that allow anatomy contacting surface 210 to conform to features such as teeth 306.

The contours, indentations, or other features of anatomy contacting surface 210 that allow support 200 to conform to bone 302 can be a patient specific support. For example, a CT scan can be used to measure and otherwise identify the contours indentations or other features of bone 302. Using the CT scan data, guide 302 can be 3D printed or otherwise manufactured such that anatomy contacting surface 210 mirrors surfaces of bone 302 and teeth 306. For instance, using CT scan data features of a mandible, such as a mental protuberance, can be mapped and the size, shape, and location of the features can be incorporated into anatomy contacting surface 210.

Using the CT scan data, X-ray data, etc., lip 304 can also be manufactured to secure support 200 to bone 302. For example, an X-ray of a patient can provide contour data for teeth 306 as well as measurements for bone 302. Using the contour data, a portion of anatomy contacting surface 210 can conform to the profile of teeth 306 and lip 304 can slide past a bottom portion of bone 302. Anatomy contacting portion 204 can be flexible to allow lip 304 to temporarily deform as support 200 is attached to bone 302. Stated another way, anatomy contacting portion 204 can flex to allow support 200 to snap into position on bone 302.

Instrument engagement portion 206 can be specific to instrument 105. For example, as shown in FIGS. 2, 3A, and 3B, instrument 105 can include a guide engagement feature that can include an arm 213, an instrument body 214, and one or more protrusions 216 that extend from instrument body 214. Instrument body 214 can include a guide surface that can define a slot 218. Still consistent with embodiments disclosed herein, the guide surface can form through holes that a drill or drill guide can engage and be secured to support 200.

Instrument engagement portion 206 can include protrusions 212, that can form a notch or other engagement features that can accept arm 213, thereby securing support 200 to instrument 105. Protrusions 216 can be sized to engage tabs 208. Contact between protrusions 216 and tabs 208 can secure support 200 in a fixed position. For example, contact between protrusions 216 and tabs 208 can prevent movement of support 200 with respect to a longitudinal axis of arm 213. For instance, protrusions 216 and tabs 208 can prevent support 200 from rotating about and/or translating along the longitudinal axis of arm 213. Stated another way, contact between protrusions 216 and tabs 208 can position slot 218 in a predetermined location and orientation relative to bone 302 or teeth 306 or other anatomy such as a knee, femur, or humeral.

Slot 218 can be a cut guide. Slot 218 can be sized to receive a blade from a saw. Once a desired location for a cut in bone 302 and/or teeth 306 is identified, data from a CT scan can be used to identify contours and other features of bone 302 and/or teeth 306 proximate the desired cut location. Using the identified contours and other features, support 200 can be 3D printed so that anatomy contacting surface 210 conforms to bone 302 and/or teeth 306 in a proper location to position slot 218 in the desired location. For example, the dimensions and other parameters of instrument body 214, protrusions 216, and slot 218 are known and can be factored into placement of protrusions 216 and tabs 208 so as to position slot 218 in the desired location.

Once support 200 is manufactured and attached to bone 302, instrument 105 can be attached to support 200. For example, as shown in FIGS. 3A and 3B, arm 213 can rest in an indentation 220 formed in support 200 such that protrusions 216 contact tabs 208. Arm 213 can be partially surrounded by protrusions 212. Protrusions 212 can grip arm 213 to secure instrument 105 in place.

Constructing support 200 and connecting instrument 105 to support 200 as disclosed herein can provide increased stability for instrument 105. Arm 104 can have a ridged nature due to the cooperation of distal joint 113, proximal arm 114, and distal arm 115. By having anatomy contacting surface 210 mirror the patient's anatomy, support 200 is less likely to slide or otherwise move with respect to the patient's anatomy. Stated another way, support 200 can provide an additional anchor point to increase the stability of instrument 105.

Figure 4A:
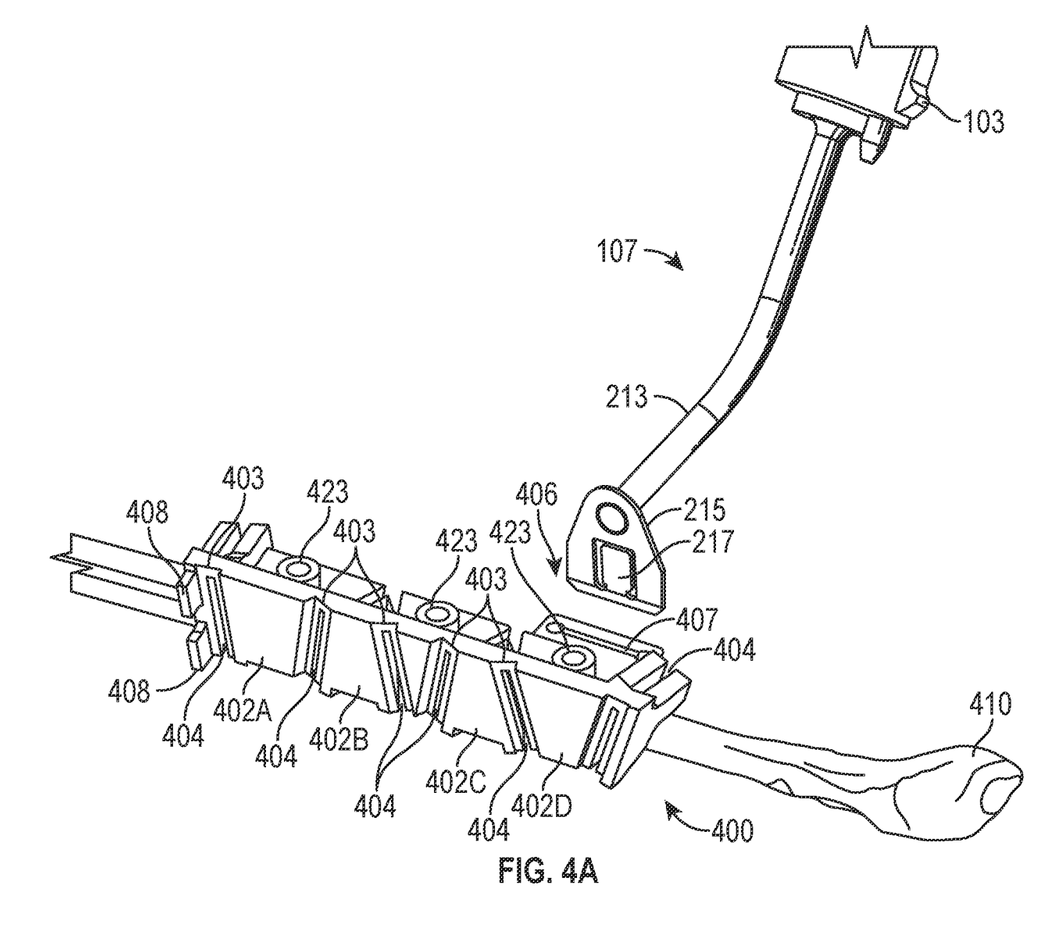
FIGS. 4A, 4B, and 4C each show a guide attached to a bone in accordance with at least one example of this disclosure.
Figure 4B:
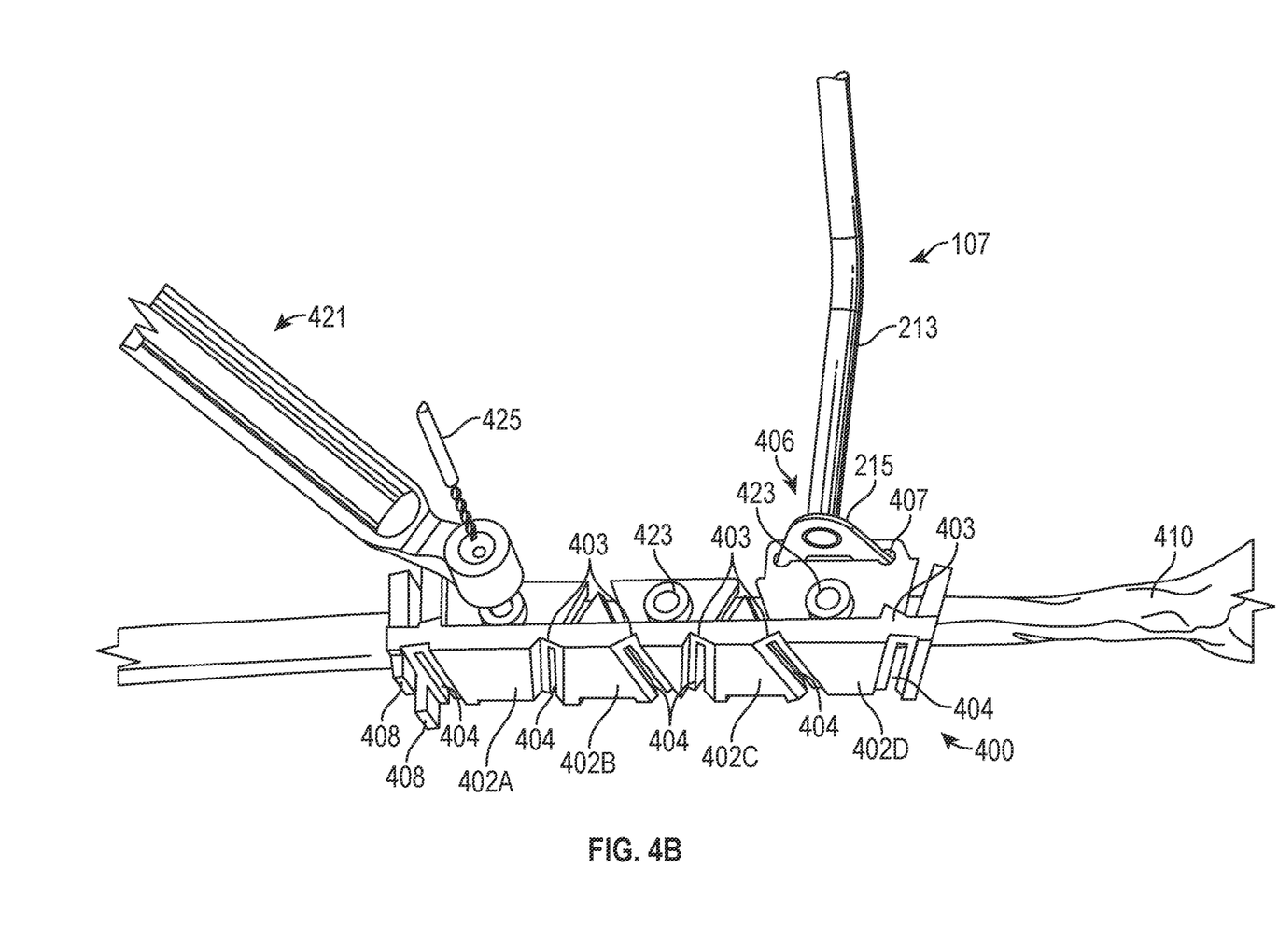
Figure 4C:
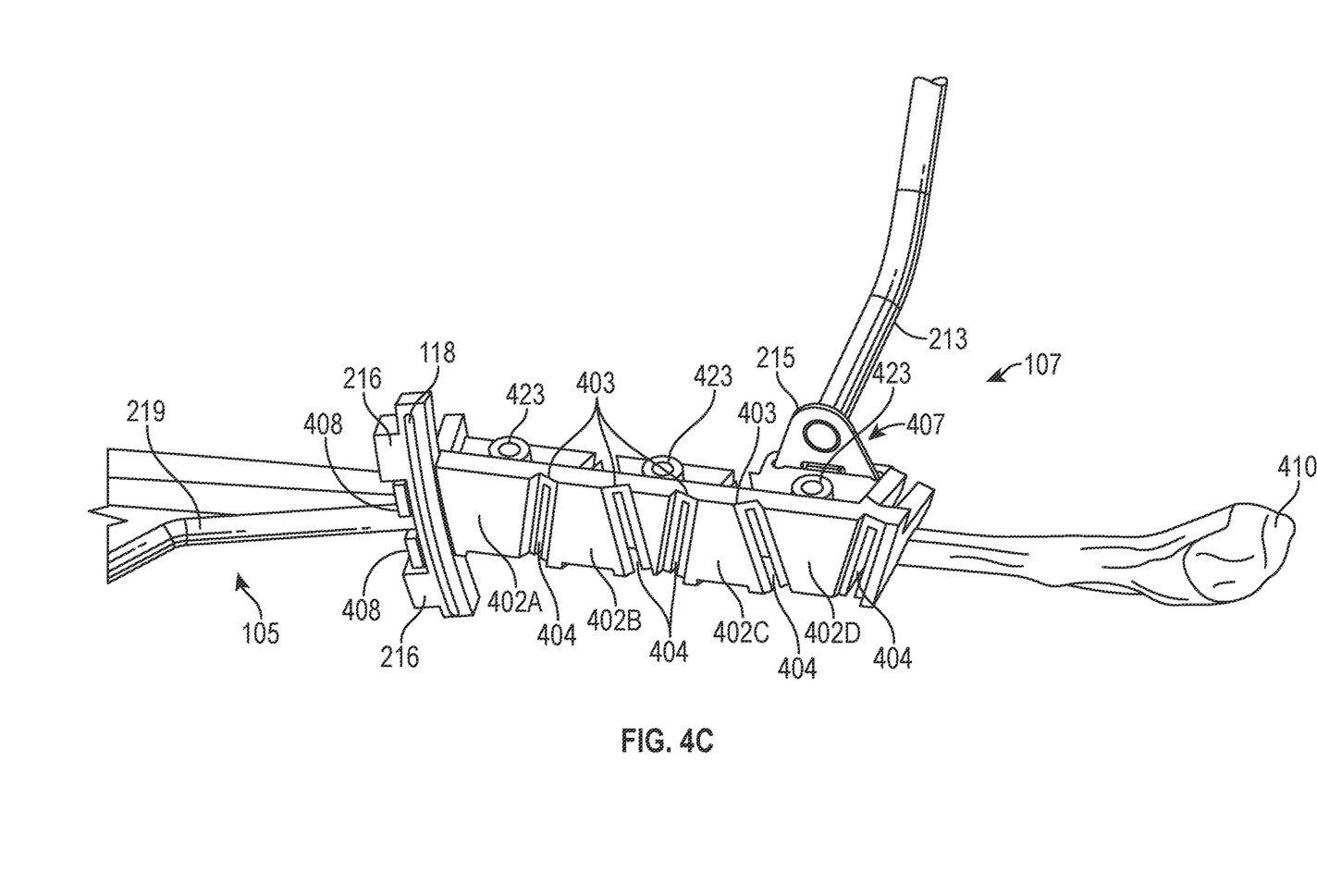

FIGS. 4A, 4B, and 4C disclose a guide 400 in accordance with at least one example of the present disclosure. Guide 400 can include a first body portion 402A, a second body portion 402B, a third body portion 402C, and a fourth body portion 402D (collectively body portions 402). One or more bridge members 403 can connect the body portions 402 together. Bridge members 403 and body portions 402 can define a plurality of slots 404. Guide 400 can also include a surgical support arm interface 406, and one or more tabs 408. Surgical support arm interface 406 can define an instrument slot 407.

FIGS. 4A, 4B, and 4C each show guide 400 attached to a bone 410 in accordance with at least one example of the present disclosure. As shown in FIGS. 4A, 4B, and 4C guide 400 can attach to bone 410, e.g., a long bone such as a fibula, femur or humerus. Each of body portions 402 can have an anatomy contacting surface and a lip as disclosed above to allow guide 400 to attached to bone 410. The anatomy contacting surfaces of guide 400 can include one or more indentations and or otherwise curved surfaces that allow the anatomy contacting surface of guide 400 to conform to one or more features of bone 410. For example, the anatomy contacting surface can include indentations or other contours that allow the anatomy contacting surfaces to conform to features such as a radial groove and/or deltoid tuberosity of a humerus or a medial lip and/or lateral lip of a femur.

The contours, indentations, or other features of the anatomy contacting surfaces that allow guide 400 to conform to bone 410 can be patient specific. For example, a CT scan can be used to measure and otherwise identify the contours indentations or other features of bone 410. Using the CT scan data, guide 410 can be 3D printed or otherwise manufactured such that the anatomy contacting surfaces mirrors surfaces of bone 410. For instance, using CT scan data features of a bone 410 can be mapped and the size, shape, and location of the features can be incorporated into the anatomy contacting surfaces.

In addition to CT scan data, X-ray data or other imaging data to design the lips and anatomy contacting surfaces so that guide 400 can be secured to bone 410 without the need for fasteners as disclosed herein. The anatomy contacting portions of body portions 402 can be flexible to allow body portions 402 to temporarily deform as guide 400 is attached to bone 410. In other words, body portions 402 can flex to allow guide 400 to snap into position on bone 410.

Surgical support arm interface 406 can be specific to instrument 105. For example, as shown in FIGS. 4A, 4B, and 4C, a cut guide holder 107 can include arm 213, a bladed portion 215 with a tab 217. After guide 400 is attached, using the patient specific features, to bone 410, bladed portion 215 can be inserted into slot 407. Tab 217 can engage an indentation or other feature within slot 407 to secure guide 400 to cut guide holder 107.

The anatomy contacting surface of guide 400 can hinder movement of guide 400 when attached to, or pressed against, bone 410 because the ridged nature of guide 400 can resist twisting or other deformation of the anatomy contacting surface. The lack of deformation can resist movement of contours of the anatomy contacting surface relative to complimentary contours of the surface of bone 410. Surgical support arm interface 406 can engage cut guide holder 107 to further position and lock guide 400, and by extension bone 410, in place. By positioning and locking guide 400 and surgical support arm 100 in place along with connecting the cut guide holder 107, stability of the cutting guide is increased. For example, the ridged nature the surgical support arms and the fixed nature of guide 400 increases stability by provide multiple anchor points, thereby limiting the degrees of freedom with which guide 400 and bone 410 are able to move. Use of the surgical support arm, such as surgical support arm 100, provides a mechanism to securely position the guide 400 against a target bone while freeing hands of the surgeon (or assistant) and allowing greater focus on the procedure.

As shown in FIG. 4B, a drill guide 421 can be positioned relative to guide 400 by a second surgical support arm. Body portions 402 each can define an opening 423. Drill guide 421 can include a protrusion or other feature that can engage any one of openings 423. The protrusion or other feature can act as a bushing so that a drill bit 425 can drill one or more holes in bone 410 without contacting guide 400. In addition to drill bit 425, drill guide 421 and openings 423 can be used to position guide rods, screws, etc. For example, using guide 400 and drill guide 421, one or more holes can first be drilled into bone 410 using drill bit 425 and then screws can be driven into bone 410 to further secure guide 400 to bone 410.

By securing bone 410 to guide 400, bone 410 can be stabilized such that should bone 410 be cut using any one of slots 404, the segmented bone fragments remain in position.

The location of openings 423 and slots 404 can be determined using CT scan data, X-ray data, or other imaging data. For example, if bone 410 is fractured. X-ray data can show the location of the fracture. When guide 400 is designed, the surgeon or other technician, can place openings 423 proximate the fracture or in other locations where bone density can allow for fasteners to securely engage bone 410. The locations of slots 404 can be determined to as to allow for bone 410 to be cut in desired locations as needed. The locations of openings 423 can also correspond to screw holes on bone plates or other fixtures to be implanted.

As shown in FIGS. 4A, 4B, and 4C, guide 400 can include tabs 408. As shown in FIG. 4C, an instrument 105 can include an instrument body 214, and one or more protrusions 216 that extend from instrument body 214. Instrument body 214 can define a slot 218. As disclosed above with respect to support 200, guide 400 can include an instrument engagement portion and protrusions that can form a notch or other engagement features that can accept arm 213, thereby securing guide 400 to instrument 105. Protrusions 216 can be sized to engage tabs 408. Contact between protrusions 216 and tabs 408 can secure guide 400 in a fix position. For example, contact between protrusions 216 and tabs 408 can prevent movement of guide 400 with respect to a longitudinal axis of arm 219. For instance, protrusions 216 and tabs 408 can prevent guide 400 from rotating about and/or translating along the longitudinal axis of arm 213.

Slot 218 can be a cut guide and sized to receive a blade from a saw. Once a desired location for one or more cuts in bone 410 are identified, imaging data can be used to identify contours and other features of bone 410 proximate the desired cut location. Using the identified contours and other features, guide 400 can be 3D printed so that the anatomy contacting surfaces conform to bone 410 in a proper location to position slot 218 in the desired location. While FIGS. 4A, 4B, and 4C show a single set of tabs 408 located near a single slot 404, guide 400 can include multiple sets of tabs 408 so that instrument 105 can be positioned so that slot 208 lines up with any number of slots 404 to allow bone 410 to be cut.

Once guide 400 is manufactured and attached to bone 410, instrument 105, cut guide holder 107, and drill guide 423 can be attached to guide 400. For example, as shown in FIGS. 4A, 4B, and 4C, protrusions 216 can cooperate with tabs 408 and blade 215 can cooperate with slot 407 to secure guide 400 and bone 410 in a desired position.

Constructing guide 400 and connecting instrument 105 and cut guide holder 107 to guide 400 as disclosed herein can provide increased stability for instrument 105 and cut guide holder 107 as well as drill guide 423. By having the anatomy contacting surfaces of guide 400 mirror the patient's anatomy, guide 400 is less likely to slide or otherwise move with respect to the patient's anatomy. Stated another way, guide 400 can provide additional anchor points to increase the stability of instrument 105 and cut guide holder 107 as well as drill guide 423.

Figure 5A:
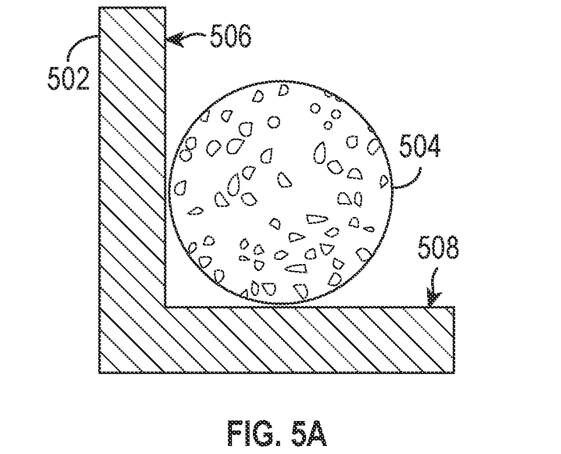
FIGS. 5A, 5B, and 5C each show a guide attached to a bone in accordance with at least one example of this disclosure.
Figure 5B:
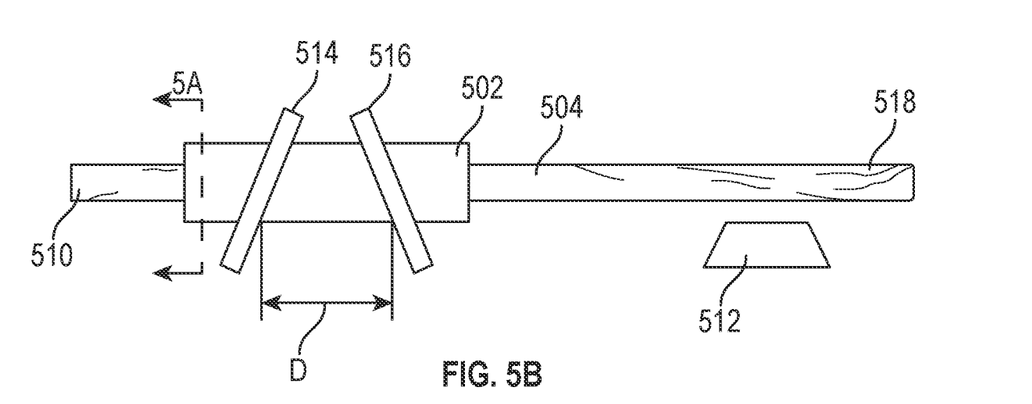
Figure 5C:
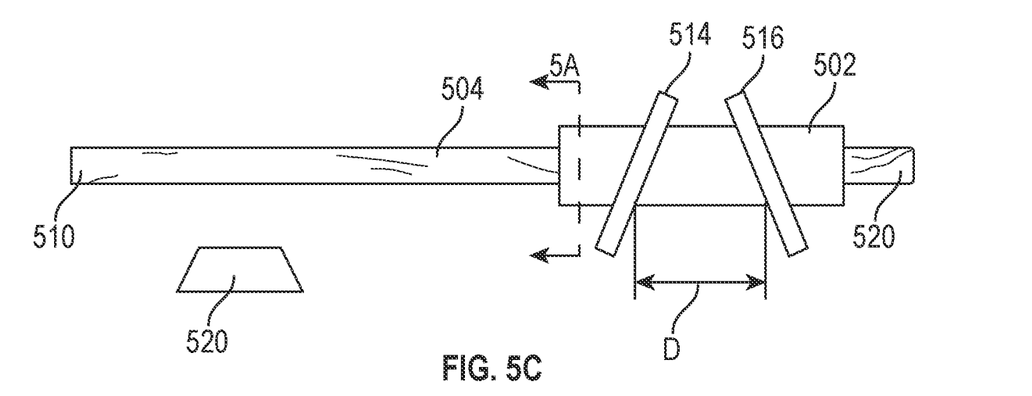

FIGS. 5A, 5B, and 5C each show a guide 502 attached to a bone 504 in accordance with at least one example of this disclosure. Guide 502 can include a first surface 506 and a second surface 508, each of which are not necessarily patient specific surface, but either or both can be patient specific. For example, if access to CT scan data, or other imaging data, is available, then either or both of first surface 506 and second surface 508 can be patient specific. If imaging data is not available, then first surface 506 and second surface 508 can be modeled using generic imaging data for a bone, such as a long bone. For instance, first surface 506 can be flat and second surface 508 (or vice versa) can contoured based on generic data for a fibula, or other long bone.

As disclosed herein, a relative distance in between cuts themselves and/or spacing in between drilled holes can be critical. If CT scan data (or other imaging data) is not available, the contours, or lack of contours, for first surface 506 and/or second surface 508 can be pre-operatively planned using a generic bone (e.g., a fibula) model. Guide 502 can be printed with a straight flat surface or surfaces instead of patient specific features. In this instance, the patient specific surface or surfaces may not be required since the pre-operatively planned relative distances between cuts and/or drilled holes can remain the same regardless of bone contours.

Because first surface 506 and second surface 508 are not patient specific, a surgeon can decide during surgery a suitable location for the resections. In other words, the natural cylindrical shape of the fibula (or other long bone) and L-shaped structure of guide 502 can allow a surgeon to select a surgeon to select a location for a cut.

FIG. 5B shows an example where guide 502 can be placed at a first location proximate a first end 510 of bone 504. As shown, during surgery, a first bone segment 512 can be cut and removed as needed. Guide 500 can define two cut slots 514 and 516. The two cuts slots 514 and 516 can be spaced a distance D apart. As shown in FIG. 5C, guide 502 can be placed at a second location proximate a second end 518 of bone 504. Guide 502 can then be used to cut a second bone segment 520. Since guide 502 defines a fixed distance D, first bone segment 512 and second bone segment 520 can have the same length and thus be similar bone segments. As such, during surgery, the surgeon can examine bone 504 during surgery and decide if first end 510 or second end 518 of bone 504 is better suited for harvesting graft material. If first end 510 is better suited, then the surgeon can cut first bone segment 512 to be used for graft material. If second end 518 is better suited, then the surgeon can cut second bone segment 520 to be used for graft material in a mandible reconstruction procedure (i.e., free fibula flap).

Figure 6:
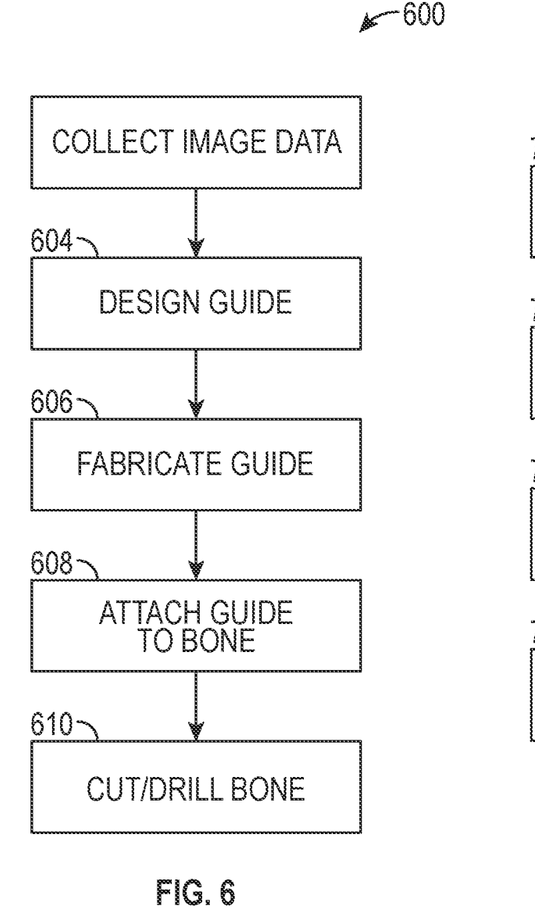
FIG. 6 shows a method in accordance with at least one example of this disclosure.

FIG. 6 shows a method 600 in accordance with at least one example of the present disclosure. Method 600 can begin at stage 602 were image data can be collected. For example, after or during examination of a patient, a physician can determine that surgery is needed. As part of the examination and/or preparing for the surgery, image data can be collected. Non-limiting examples of collecting imaging data can include taking X-rays, performing CT scans, MRI scans, etc. The image data can be used to identify shapes, contours, protrusions, abnormalities, fractures, or damage to bone.

Using the collected image data one or more guides, such as support 200 and guide 400 disclosed herein, can be designed (604). Designing a guide can include specifying contours, recesses, protrusions, and other shapes for an anatomy contacting surface as well as any lips that can be part of the guides so that the anatomy contacting surface and the lips conform to the patient's anatomy.

Designing the guides can include selecting the location for slots that may be needed to allow bone to be cut. Designing the guides can include specifying the location of any openings that are needed for drill bit placement and/or to guide screws, rods, and/or pins.

During the design phase, the location of tabs and other instrument engagement features can also be specified. For example, knowing that dimensions of the various instruments, such as instrument 105, cut guide holder 107, and drill guide 423, the tabs, openings, cutting slots, etc. can be set so as to accommodate any offsets that are needed to allow the instruments to properly connect to the guides.

Designing the guides can be accomplished using a variety of design tools. For example, computer aided design (CAD) programs can be used to generate solid models of both the patient's anatomy as well as the guides. For instance, using the image data, a 3D rendering of the patient's anatomy can be generated and the guides designed around the 3D rendering.

Once the guides are designed, the guides can be fabricated (606). Fabricating the designs can be done using a variety of manufacturing processes. For example, the guides can be 3D printed. Using 3D printers to print polymer guides can result in reduced cost as well as lower lead times. In addition, the 3D printed guide can be used as part of a casting process if metal guides are needed. For example, a polymer 3D printed guide can be used as part of a lost foam casting process where the polymer is melted away or otherwise destroyed when a molten metal is poured into a mold. The cast guide can then be machined as needed to prepare the guide for surgery.

Once the guides have been fabricated it can be attached to bone (608). For example, and as disclosed herein, once fabricated, the guides can be placed in contact with the patient's anatomy. As disclosed herein, the guides can attach to teeth, a mandible, a humerus, a femur, etc. The anatomy contacting surfaces can engage teeth, or other bones such that the anatomy contacting surfaces at least partially surround parts of the patient's anatomy so as to secure the guides to the teeth or bones.

Attaching the guides to the bone can also include attaching instruments to the guide. For instance, the surgical support arm and be positioned and locked into place by pushing a button, such as button 103. While positioning surgical support arm or after surgical support arm is positioned, instruments can be attached to the guide to assist in holding the guide and/or bone to which the guide is attached in place. As disclosed herein, the tabs, protrusions, and slots of the guide can engage the instruments to secure the instruments to the guide and provide additional points of fixation to minimize movement of the bone and/or guides during surgery.

By positioning and locking the surgical support arm in place along with connecting the instrument to the guide, stability can be increased. For example, the ridged nature of when coupled to the support, the surgical support arm and the support can position the instrument and a guide surface in a predetermined location and orientation relative to the anatomical surface of the patient. The increased stability can result from the ridged nature of the surgical support arm along with cooperation of the anatomy contacting surface hindering movement of the guide relative to the bone. Stated another way, the surgical support arm and the guide can provide multiple anchor points, thereby limiting the degrees of freedom within the system and increasing stability and/or rigidity as compared to use of the guide or surgical support arm alone in positioning a cut guide.

After attaching the guides, the bone can be cut and/or drilled (610). For instance, if only the guides are attached to the bone, the bone can be drilled to accept screws, rods, and/or pins using openings in the guide and drill guides as a guide. The bone can also be cut using slots formed in the guide as well as slots formed in the instruments.

Figure 7:
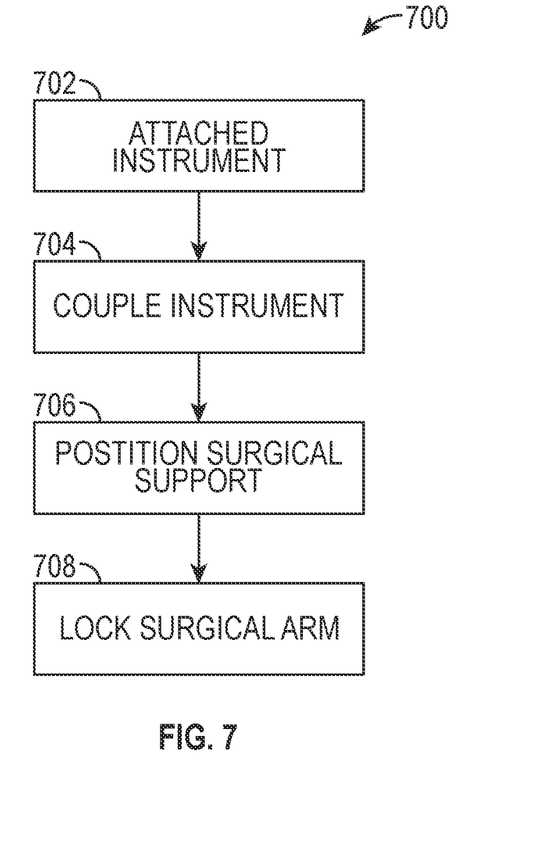
FIG. 7 shows a method in accordance with at least one example of this disclosure.

FIG. 7 shows a method 700 in accordance with at least one example of the present disclosure. Method 700 can be a standalone method or a subroutine of method 600. For example, method 700 can be a routine for attaching a guide or support in stage 608. Method 700 can begin at stage 702 were an instrument can be attached to a surgical support arm. For example, an instrument, such as instrument 105, cut guide holder 107, or drill guide 423 can be attached to surgical support arm 104. The instrument can be coupled to an instrument interface of the patient-specific guide or patient-specific support (704). For example, the instrument can be coupled to support 200 or guide 400 as disclosed herein.

Surgical support arm and a patient-specific guide or support can be positioned to engage anatomical feature of patient (706). For example, the surgical support arm and the patient-specific guide or support can be position so the anatomy contacting surface of the guide or support can rest against or proximate the anatomy of the patient as disclosed herein.

After the surgical support arm and guide or support are positioned, the surgical support arm can be locked (708) to maintain position of the patient-specific guide with respect to anatomical feature. By positioning and locking the surgical support arm in place along with connecting the instrument to the guide, stability can be increased. The increased stability can result from the ridged nature of the surgical support arm along with cooperation of the anatomy contacting surface hindering movement of the guide relative to the bone. Stated another way, the surgical support arm and the guide can provide multiple anchor points, thereby limiting the degrees of freedom within the system and increasing stability and/or rigidity as compared to use of the guide or surgical support arm alone in positioning a cut guide.

As disclosed herein, the various stages of method 600 and 700 can be rearranged and/or omitted without departing from the score of this disclosure. For example, the surgical support arm can be position (706) before the instrument is attached (702).

Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical system comprising:
   a surgical support arm including a plurality of lockable joints configured to maintain a position of a distal end of the surgical support arm;
   an instrument including a guide surface, the instrument coupled to the distal end of the surgical support arm; and
   a patient-specific support comprising an instrument engagement portion and an anatomy contacting surface, the instrument engagement portion configured to receive a portion of the instrument and the anatomy contacting surface contoured to match a contour of an anatomical surface of a patient,
   wherein, when coupled to the patient-specific support, a surgical support arm and the patient-specific support position the guide surface of the instrument in a predetermined location and orientation relative to the anatomical surface of the patient.

2. The surgical system of claim 1, wherein the instrument engagement portion comprises a channel sized to receive the portion of the instrument.

3. The surgical system of claim 1, wherein the instrument engagement portion includes a tab and the portion of the instrument includes a protrusion, the tab sized to engage the protrusion.

4. The surgical system of claim 1, wherein the instrument engagement portion includes a plurality of protrusions arranged to engage the portion of the instrument.

5. The surgical system of claim 1, wherein the instrument engagement portion defines a through hole sized to receive a drill guide.

6. The surgical system of claim 1, wherein the instrument engagement portion defines a slot sized to receive a cut guide.

7. The surgical system of claim 1, wherein the anatomy contacting surface forms a lip sized to engage a portion of the anatomical surface.

8. The surgical system of claim 1, wherein the patient-specific support defines a cut slot.

9. The surgical system of claim 1, further comprising the surgical support arm.

10. The surgical system of claim 1, wherein the guide surface of the instrument defines a cut slot.

11. The surgical system of claim 1, wherein the patient-specific support further comprises a second instrument engagement portion.

12. The surgical system of claim 1, wherein the anatomy contacting surface is contoured to engage at least one structure selected from a group of structures including:
    teeth; and
    a mandible.

13. The surgical system of claim 1, wherein the anatomy contacting surface is contoured to engage a long bone.

* * * * *